United States Patent [19]
Ward et al.

[11] Patent Number: 5,711,861
[45] Date of Patent: Jan. 27, 1998

[54] DEVICE FOR MONITORING CHANGES IN ANALYTE CONCENTRATION

[76] Inventors: W. Kenneth Ward, 365 SW. Breeze Ct., Portland, Oreg. 97225; Eric S. Wilgus, 2207 NE. 12th Ave., Portland, Oreg. 97212

[21] Appl. No.: 561,972

[22] Filed: Nov. 22, 1995

[51] Int. Cl.$^6$ .................................................. G01N 27/26
[52] U.S. Cl. .................. 204/403; 204/415; 435/287.1; 435/289.1; 435/817; 128/642
[58] Field of Search .......................... 204/415, 403; 422/68.1, 82.03, 82.01; 435/288, 291, 817; 128/635, 642

[56] References Cited

U.S. PATENT DOCUMENTS

| | | | |
|---|---|---|---|
| 3,542,662 | 11/1970 | Hicks et al. | 204/195 |
| 3,996,141 | 12/1976 | Updike | 210/22 |
| 4,240,438 | 12/1980 | Updike et al. | 128/635 |
| 4,340,458 | 7/1982 | Lerner et al. | 204/195 R |
| 4,431,004 | 2/1984 | Bessman et al. | 128/635 |
| 4,436,094 | 3/1984 | Cerami | 128/635 |
| 4,650,547 | 3/1987 | Gough | 204/1 T |
| 4,682,602 | 7/1987 | Prohaska | 128/635 |
| 4,721,677 | 1/1988 | Clark, Jr. | 435/291 |
| 4,757,022 | 7/1988 | Shults et al. | 435/291 |
| 4,813,424 | 3/1989 | Wilkins | 128/635 |
| 4,832,797 | 5/1989 | Vadgama et al. | 204/1 T |
| 4,871,440 | 10/1989 | Nagaya et al. | 204/403 |
| 4,890,620 | 1/1990 | Gough | 128/635 |
| 4,909,908 | 3/1990 | Ross et al. | 204/403 |
| 4,919,141 | 4/1990 | Zier et al. | 128/635 |
| 4,923,586 | 5/1990 | Katayama et al. | 204/403 |
| 4,935,345 | 6/1990 | Guilbeau et al. | 435/817 |
| 4,969,468 | 11/1990 | Byers et al. | 128/642 |
| 4,986,271 | 1/1991 | Wilkins | 128/635 |
| 4,994,167 | 2/1991 | Shults et al. | 204/403 |
| 5,089,112 | 2/1992 | Skotheim et al. | 204/403 |
| 5,165,407 | 11/1992 | Wilson et al. | 128/635 |
| 5,262,305 | 11/1993 | Heller et al. | 204/403 |
| 5,264,103 | 11/1993 | Yoshioka et al. | 204/403 |
| 5,286,364 | 2/1994 | Yacynych et al. | 204/418 |
| 5,322,063 | 6/1994 | Allen et al. | 204/403 |
| 5,337,747 | 8/1994 | Neftel | 128/635 |
| 5,372,133 | 12/1994 | Esch | 128/631 |
| 5,387,327 | 2/1995 | Khan | 204/403 |
| 5,395,504 | 3/1995 | Saurer et al. | 204/403 |

*Primary Examiner*—Bruce F. Bell
*Attorney, Agent, or Firm*—Kolisch, Hartwell, Dickinson, McCormack & Heuser

[57] ABSTRACT

The invention provides an electrochemical sensor system for measuring analyte concentrations in a sample fluid. The invention is particularly useful for measuring analytes such as glucose in a patient. An implantable glucose sensor includes a disc-shaped body containing multiple anodes on opposing sides of the body. Electrodes are connected to a transmitter which transmits radio signals to an external receiver and computer where data is processed to yield relative glucose concentration figures.

22 Claims, 8 Drawing Sheets

DEVICE FOR MONITORING CHANGES IN ANALYTE CONCENTRATION

FIELD OF THE INVENTION

The invention relates to electrochemical systems for measuring analyte concentration. In particular, the invention involves a sensor including electrodes under a semi-permeable membrane for monitoring analyte concentrations in fluids surrounding the sensor.

BACKGROUND

There are many instances when it is necessary to monitor the concentration of molecules ("analytes") in a fluid. For example, glucose levels must be frequently monitored in persons with diabetes so that appropriate doses of insulin can be administered in a timely manner. Many other analytes are measured commonly in human blood and in other fluids.

A variety of methods and devices for measuring analytes in fluids have been devised. One such device, referred to as an electrochemical sensor, typically includes oppositely charged electrodes under a semi-permeable membrane. Depending on what analyte is being monitored, membranes, enzymes and/or other appropriate materials are provided around the electrodes so that analyte reaction and transport from the fluid surrounding the sensor is controlled. Oxidative and reductive reactions take place at or near the electrodes, thus causing electron potentials measured as changes in current which may be correlated to the concentration of analyte in the fluid.

Electrochemical sensors have been used to measure glucose in human blood for a long time. Most of these sensors are designed to measure glucose in a blood sample which has been drawn or extracted from the patient. For patients such as people with diabetes who must test blood glucose levels as often as several times per day, the regular blood drawing process (typically by finger tip puncture) becomes quite cumbersome, messy and even painful. The diabetic must carry special equipment for extracting blood. Some patients fail to test as frequently as they should because of problems associated with the blood extracting process.

Therefore, it has been recognized for a long time that an implanted glucose sensor would offer the important advantage of avoiding the need for repeated blood extraction. However, there are other problems which must be addressed with an implantable sensor. First, there must be a mechanism for accessing raw electrical data generated by the sensor under the patient's skin. Protruding wires are undesirable because they are cumbersome, prone to causing infection and sometimes painful. Accordingly, it is preferable to include a wireless data transmission (telemetry) device coupled to the sensor in a single implantable unit so that no trans-dermal wires are required.

Second, an implanted sensing unit may cause internal trauma, i.e., bruising or bleeding from the patient's routine movement or contact with his or her environment, especially if the sensing unit is large or thick or if it is geometrically shaped with any sharp points or edges.

Another problem associated with implantable sensors is that over time (days and weeks) a cellular coat tends to develop around the sensor which may eventually block the analyte of interest from contacting the electrodes, thus causing the sensor to fail.

For these reasons, and perhaps other reasons, researchers in the field have been unsuccessful in their attempts to produce an implantable sensor unit which is capable of functioning satisfactorily for a sufficient period of time to justify the expense and inconvenience of producing and surgically implanting the sensing hardware.

A viable implantable glucose sensor should provide reliable performance for at least 1–2 months, preferably three months or more. During its useful life, the device should generate a predictable dose response over a concentration range of approximately 40 to 400 milligrams per deciliter (mg/dl). The device should exhibit a lag time between a concentration change and the resulting signal output of less than 20 minutes, preferably less than 10 minutes. The sensor should be relatively insensitive to potential interfering substances such as ascorbic acid and acetaminophen. The device should be relatively accurate for at least several days after calibration (stability). Glucose measurement with the sensor should be precise to at least within approximately 10 mg/dl. The sensor should be incorporated in an implantable unit which is capable of wireless data transmission, and which is dimensioned so as to minimize surgical complication and risk of pain, bruising or other internal trauma.

SUMMARY OF THE INVENTION

The objectives stated above are achievable with the device and system of the present invention which includes a device for electrochemically sensing changes in the concentration of an analyte of interest.

In one embodiment of the invention, the device includes a sensor body having two opposing sides. Each side of the body includes at least one, preferably several, anode(s) and at least one cathode spaced apart from each other and covered by a membrane which is semi-permeable to the analyte of interest. In a preferred sensor design for measuring glucose, plural anodes are disposed on two opposing sides of a disc-shaped sensor body. The anodes are covered by an enzyme layer including glucose oxidase and an outer semi-porous membrane layer made of a material such as Parylene™ ("PPX") or Chronoflex™ AR ("CAR").

In another embodiment of the invention, the sensor body contains a plurality of electrode pairs, each pair including an anode and a cathode. The electrode may take the form of points or lines. In one design linear electrodes are arranged in a "spoke-like" configuration. The electrode pairs preferably are disposed on both sides of the body.

An implantable glucose sensor, according to the present invention, may be electrically coupled to a transmitter which includes a power source, for example a battery. The transmitter is capable of converting data signals from the sensor into corresponding radio signals. A receiver is provided remotely from the sensor for receiving the radio signals. A processor is connected to the receiver and used to interpret the radio signals, to yield analyte concentration figures.

The present invention also provides a method of making an analyte sensor. A substantially disc-shaped body is provided with two opposing sides. At least one cathode and plural anodes are created on each side of the body. A semi-permeable membrane is deposited on the electrodes. When the method is employed to make a glucose sensor, the enzyme layer including glucose oxidase is created between the anodes and the semi-permeable membrane. An interferent retarding layer may be created between the anodes and the enzyme layer.

Definitions

Figure 1:
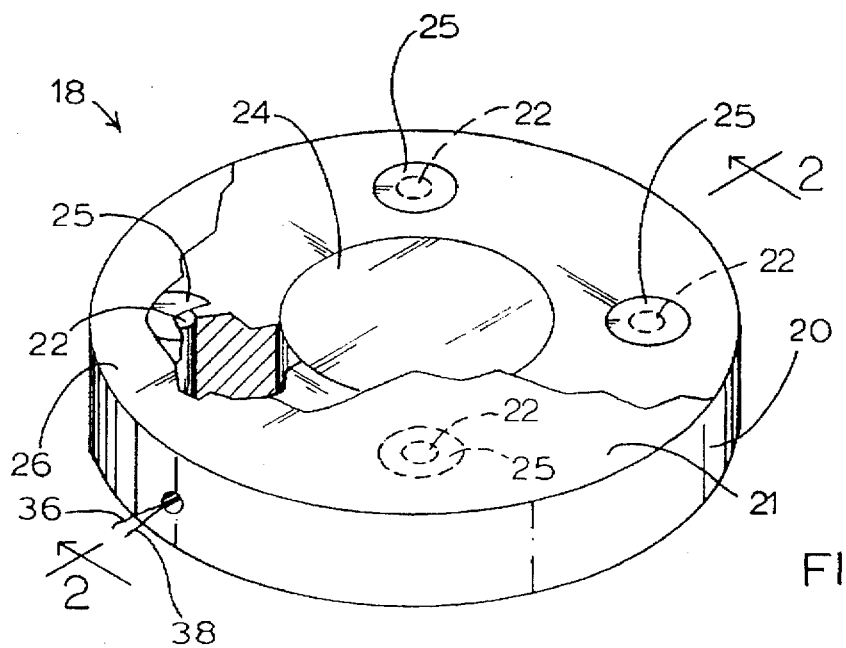
FIG. 1 is a partially cut-away perspective view of an analyte sensor in accordance with a preferred embodiment of the present invention.

An electrode means an electric conductor, which may be an anode or a cathode.

An anode is a positively charged conductor.

A cathode is a negatively charged conductor.

A sensor is a device which detects changes in analyte concentration in a fluid surrounding the sensor. A sensor includes an anode and a cathode, chemically modified and physically arranged to produce electric signal changes which can be interpreted by sensing electronics into analyte concentration changes over a specified concentration range.

An analyte is a molecule of interest in a fluid surrounding a sensor.

An electrometer is a device which senses small changes in current and translates amps to volts.

A transmitter or radio telemetry device is a device which transmits radio signals.

A receiver is a device capable of receiving radio signals from a transmitter.

A body is a housing for supporting and containing sensor components.

A semi-permeable membrane or analyte selective coating is a material which permits controlled transfer of an analyte through the material.

Interfering substances are molecules in the fluid surrounding the sensor, which are potentially detectable by the sensor possibly causing an inaccurate or erroneous analyte concentration determination. An interferent retarding layer is a material employed in a sensor to either physically or chemically neutralize a potential interfering substance, thereby preventing the substance from interfering with the desired analyte concentration determination.

Chronoflex™ ("CAR") is a trade name for a carbonate based polyurethane available from Polymedica.

Parylene™ ("PPX") is a trade name for polyparaxylxylene available from Union Carbide.

DESCRIPTION OF THE INVENTION

We have invented an analyte sensing system including an implantable sensor which exhibits significantly improved performance characteristics over a longer functional life in comparison to prior sensing systems. Our invention has also resulted in improvements which are useful in non-implantable sensors and other sensing applications. The model for illustrating important principles of the present invention, as discussed in detail below, relates to implantable glucose sensors.

Prior implantable glucose sensors do not function satisfactorily over a long enough period to justify the cost and complications of implantation. We have observed that increasing the number of anodes, or electrode pairs, or total number of sensors connected in parallel, and by distributing the anodes on different sensing faces of one or more sensors, greatly enhances the functional life span of an implantable glucose sensing system. Our experiments confirm that redundancy enhances sensor unit function. Other problems with prior electrochemical glucose sensors relate to electrical drift and instability. The redundancy of the present invention, i.e., multiple anodes or multiple sensors distributed on multiple faces of one device, appears to significantly reduce such drift. A possible reason for this is that each individual sensing unit may have its own fundamental instability, and that by incorporating multiple sensing units into a single system, an averaging effect tends to cancel out random drift associated with individual sensors.

Figure 2:
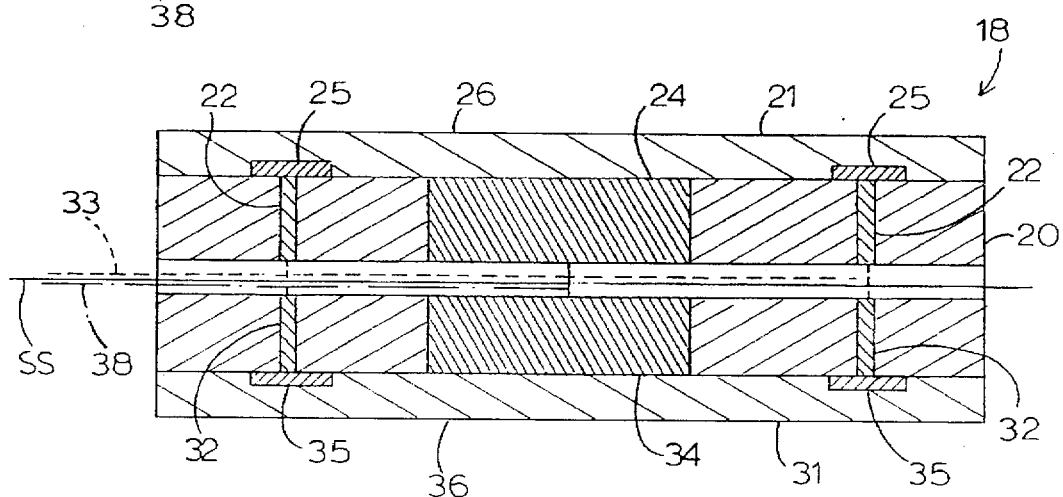
FIG. 2 is a cross-sectional view of the sensor shown in FIG. 1.

FIGS. 1 and 2 illustrate a disc-shaped glucose sensor which has two opposing faces, each of which has an identical electrode configuration. One of the faces can be seen in the partially cut-away perspective view in FIG. 1. Sensor 18 includes a disc-shaped body 20. On planar face 21 of sensor 18, four platinum anodes 22 are symmetrically arranged around centrally disposed silver chloride cathode 24. Each anode 22 is covered by an enzyme layer 25 including the active enzyme glucose oxidase and stabilizing compounds such glutaraldehyde and bovine serum albumin (BSA). A semipermeable membrane layer 26 covers all of the electrodes and individual enzyme layers. The thickness and porosity of membrane layer 26 is carefully controlled so as to limit diffusion and/or transport of the analyte of interest (glucose) from the surrounding fluid into the anode sensing regions. The mechanism of selective transport of the analyte of interest through the membrane may involve one or more of the following principles: molecular size exclusion, simple mass transfer, surface tension phenomena and/or other chemically mediated processes.

A cross-section of sensor 18 is shown in FIG. 2. Sensor 18 has a plane of symmetry SS which is normal to the plane of the figure. Under face 31 of sensor 18 anodes 32 are spaced equidistantly apart from cathode 34. Enzyme layers 35 cover anodes 32. A semipermeable membrane 36, preferably PPX or CAR, covers the enzyme layers and electrodes. Each of anodes 22 and 32 are connected to a common anode wire 37 which leads out of the sensor for electrical connection to an electrometer. Similarly, each of cathodes 24 and 34 are connected to a common cathode lead 38 which leads out of sensor 18 for electrical connection to the electrometer.

Figure 3:
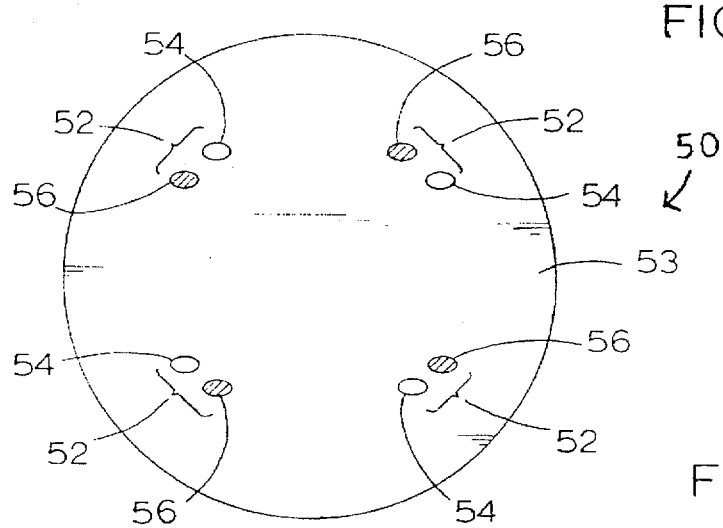
FIG. 3 is a top view of an analyte sensor in accordance with a second embodiment of the present invention.

FIG. 3 shows an alternative embodiment of the invention in which a plurality of electrode pairs are presented on both sides of a disc-shaped sensor. Only one side of the sensor is shown in FIG. 3. The enzyme and semipermeable membrane layers are removed to permit viewing of the electrode configuration. Sensor 50 (an "8-in-1 sensor") includes eight electrode pairs 52, only four of which are shown distributed around surface 53 of sensor 50. Each electrode pair 52 includes an anode 54 spaced apart from a cathode 56. Similar to the first embodiment described, all of anodes 54 are linked to a common anode wire (not shown) which extends outside the body of sensor 50. All of cathodes 56 are connected to a common cathode wire which extends outside sensor 50. The anode and cathode wires leading out of sensor 50 are eventually connected to an electrometer.

Figure 4A:
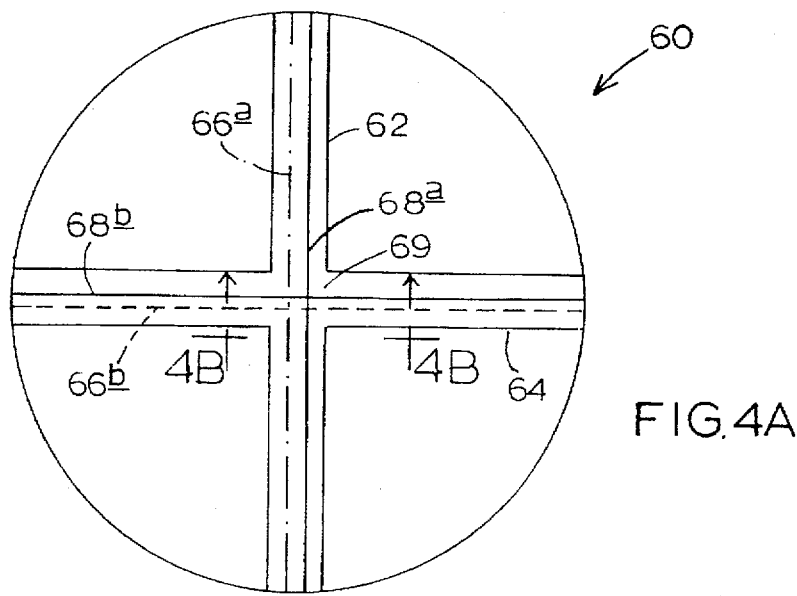
FIG. 4A is a top view of an analyte sensor employing linear electrodes in accordance with a third embodiment of the present invention.
Figure 4B:
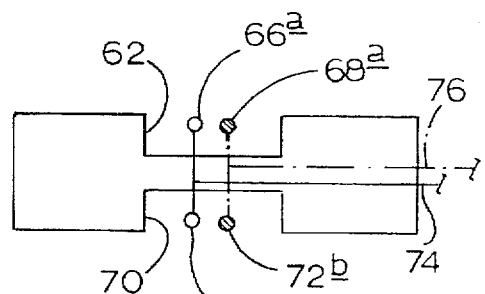
FIG. 4B is a partial cross-sectional view of the sensor shown in FIG. 4A.
Figure 5:
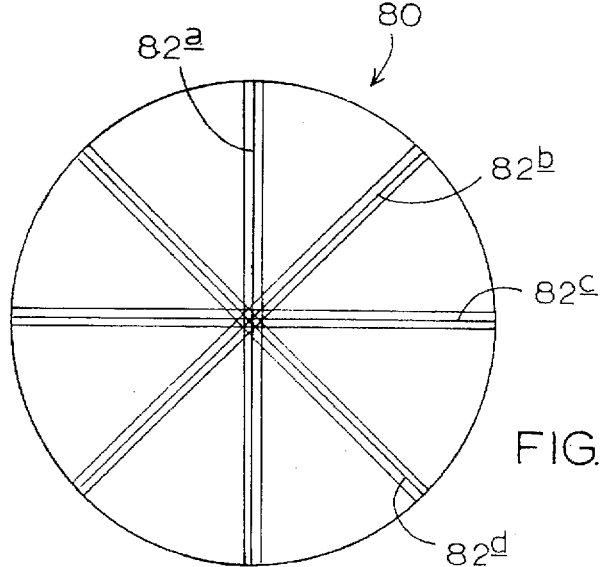
FIG. 5 is a top view of another analyte sensor in accordance with a fourth embodiment of the present invention.

FIGS. 4A, 4B and 5 illustrate a different type of anode and cathode configuration in which each electrode is exposed along a linear path on the sensor surface. In FIG. 4A, sensor 60 is formed with troughs 62 and 64 that intersect at right angles in the center of the sensor surface. Within trough 62 linear anode 66a runs parallel to linear cathode 68a. Similarly, in trough 64 linear anode 66b runs parallel to linear cathode 68b. The electrodes are insulated from each other in the junction area 69 where the troughs intersect. FIG. 4B shows a cross section through trough 62 in the junction area of the sensor. Trough 62 has a corresponding trough 70 on the opposite side of sensor 60. In trough 70, linear anode 72a runs parallel to linear cathode 72b. Anodes 66a and 72a are both connected to common anode wire 74. Linear cathodes 68a and 72b are connected to common cathode wire 76. Anode wire 74 and cathode wire 76 lead out of sensor 60 for connection to an electrometer. The troughs are preferably filled with an electrolyte gel.

As shown in FIG. 5, the concept of employing linear electrodes across opposing faces of the sensor can be extended to provide more electrode sensing area or "spokes". In FIG. 5 sensor 80 is essentially the same as sensor 60 (FIGS. 4A and 4B) except that it has two additional troughs, each containing another pair of parallel linear electrodes. Sensor 80 includes trough 82a, 82b, 82c and 82d, all of which intersect in the center of sensor 80. Each of the troughs 82a–d contains a pair of linear electrodes (anode and cathode) encased in electrolyte gel. All of the linear anodes in sensor 80 are connected to a common anode wire, and all of the linear cathodes are connected to a common cathode wire. Other anode patterns which function effectively include a circle, concentric circles or a spiral.

Figure 6:
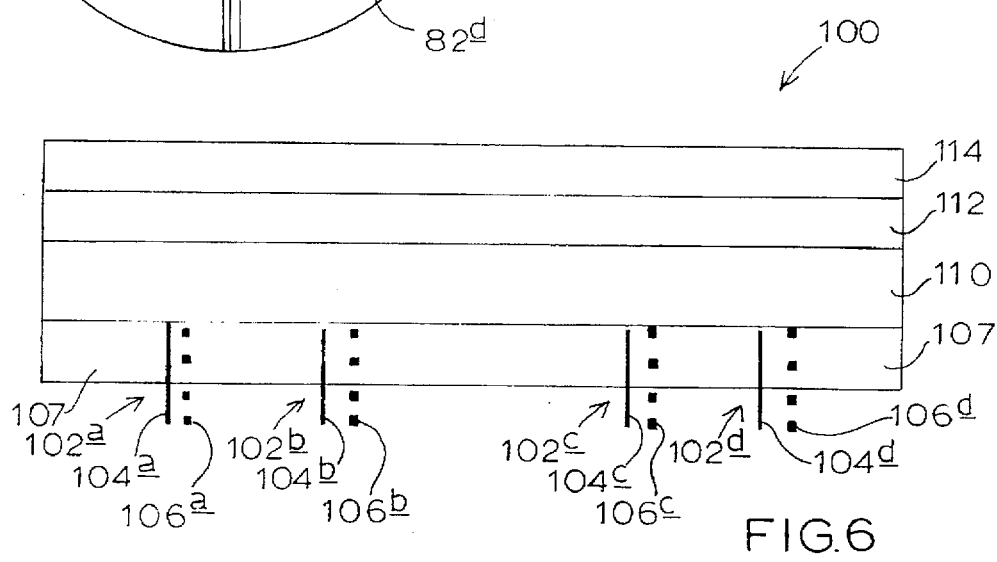
FIG. 6 is a schematic side view of a glucose sensor including an interferent retarding layer.

FIG. 6 shows schematically a cross section through multiple layers on one side of a sensor. Sensor 100 includes an electrode configuration similar to the embodiment illustrated in FIG. 3. Electrode pairs 102a–102d each include a cathode 104a–104d and an anode 106a–106d, respectively.

An electrolyte gel 107 surrounds the anode-cathode pairs, thus providing a faster and more sensitive response to changes in glucose concentration. The gel may be produced from methacrylate compounds or from collagen. For example, a methacrylate compound may be dissolved in an organic solvent and then deposited around the anode-cathode pairs. The solvent is then evaporated. Phosphate buffered saline with KCl is then added to the gel to swell the methacrylate compound. In the 8-in-1 embodiment (FIG. 3), the electrolyte gel is placed over the surface of the electrode pairs and/or the gel is injected into the drilled cylinder in which the electrode pair is situated. Similarly, in the radial spoke-type embodiments shown in FIGS. 4 and 5, the troughs may be filled with electrolyte gel.

Layer 110 is deposited immediately on top of the electrodes for the purpose of minimizing or avoiding interference due to the presence of interfering substances which may be present in the sample fluid. Enzyme layer 112 is deposited on top of interferent retarding layer 110. Enzyme layer 112 includes, in the case of a glucose sensor, glucose oxidase, and is applied in a solution of glutaraldehyde and bovine serum albumin (BSA), either by placement of a drop over each electrode pair, or by dip-coating the entire sensing unit, or by spin-coating. Semi-permeable membrane 114 is deposited on top of enzyme layer 112 for the purpose of controlling diffusion of glucose from the sample fluid into the electrode region of the sensor. PPX at a thickness of about 3,000–6,000 angstroms works well for this purpose. The preferred thickness of PPX layer 114 is 4,000–5,000 A. Other suitable materials for semi-permeable membrane 114 include CAR and polyurethanes such as Tecoflex™, Techothane™, Carbothane™ and Cook™ composite.

A number of interferents which exist in human plasma, can be oxidized at the anode when connected to sensor electronic circuitry, thus registering a current which interferes with the signal of interest, i.e., signal generated due to the presence of glucose. Potential interferents include, for example, uric acid, ascorbic acid and the common analgesic drug acetaminophen. Interferents tend to pass freely through semi-permeable membrane 114 and enzyme layer 112. The compounds can be blocked from reaching the electrodes by interfering retarding layer 110 which has a pore size big enough to allow diffusion of hydrogen peroxide ($H_2O_2$), a product of glucose oxidation in layer 112, yet small enough to exclude compounds such as uric acid, ascorbic acid and acetaminophen from reaching the electrodes.

A preferred material for the interferent retarding layer 110 is PPX. PPX is a hydrophobic compound which is applied to the substrate in a vacuum deposition chamber. The deposition process can be carefully regulated to form an interferent retarding layer of precise thickness (5,000–8,000 A) prior to depositing the enzyme layer. CAR also appears to be a suitable material for use as an interferent retarding layer.

Paired sensors can also be used to provide an alternate method of avoiding interfering currents from oxidizable, non-glucose compounds. For example, a first sensor is a standard sensor with glucose oxidase. The first sensor measures glucose and interfering compounds. A second sensor is the same as the first sensor except it does not have glucose oxidase and thus detects only the interfering compounds. The magnitude of the current from the second sensor is subtracted from the magnitude of the current from the first sensor to yield a signal which represents the glucose concentration independent from interfering substance concentrations.

The sensor designs described above can also be modified so that the electrodes detect fluctuations in oxygen concentration which is relatable to glucose concentration. In this approach, the sensor monitors oxygen disappearance instead of hydrogen peroxide appearance. First, the polarity is changed so that the platinum electrodes (previously referred to as "anodes") become negatively charged with respect to the silver chloride (previously referred to as the "cathode"), i.e., the platinum becomes the cathode and the silver chloride becomes the anode. Second, a membrane is deposited immediately on top of the cathode and anode which is permeable to oxygen but not to larger molecules. The outer membrane and the enzyme layer remain the same. In this configuration, glucose concentration results in a decrease in oxygen concentration at the negatively charged electrode.

Another embodiment of the invention has a modified outer membrane. It is possible that functional longevity of implantable sensors is limited because the outer membrane tends to become "fouled," i.e., plugged or covered by molecules and/or other cellular materials. Accordingly, one adaptation of the invention employs a changing membrane so that the outer membrane can be renewed over time without disrupting operation of the sensor. In the modified sensor, the outer membrane is a solid sheet which can be moved across the face of the sensor where the electrodes are exposed. For example, the membrane can be transferred from one roller to another roller analogous to the way film is transferred inside a camera. A drive mechanism such as a small motor may be included in the implantable unit for driving the rollers.

Figure 7:
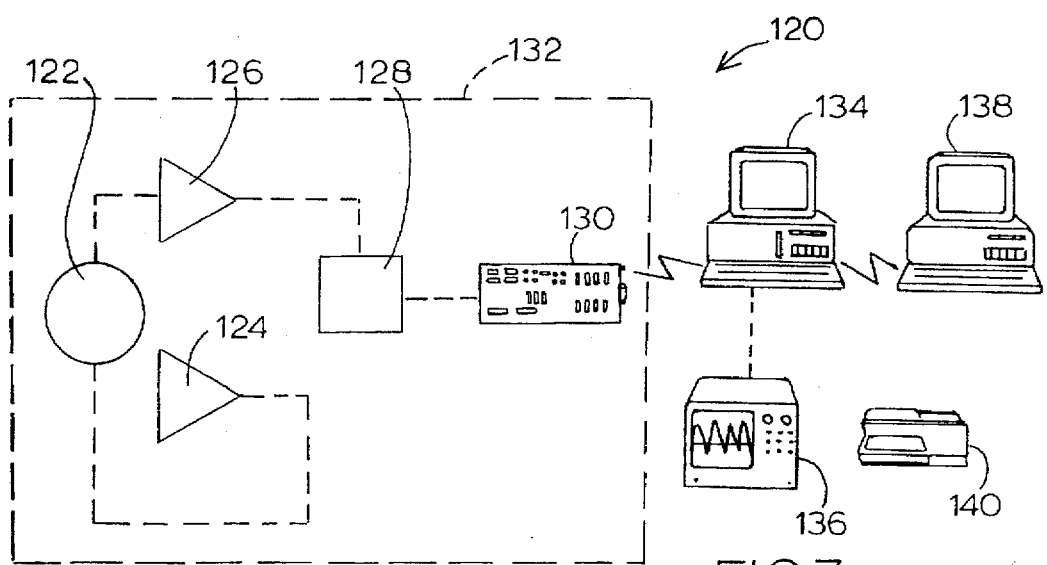
FIG. 7 is a schematic flow chart of an analyte monitoring system including sensor, electronics, telemetry and computing components.

FIG. 7 shows schematically how an implantable glucose sensor is connected in a glucose monitoring system 120. Electrodes in sensor 122 are polarized by polarizing circuit 124. Polarization of the sensor electrodes may be constant or pulsed. Our experiments have shown improvement in sensor performance stability, i.e., maintaining sensitivity and minimizing drift, when polarization is pulsed. For example, polarization of the sensing electrodes can be pulsed alternately on and off at intervals of 15 milliseconds. It may also be advantageous to alternate polarization, i.e., switch the charge of each electrode at regular intervals.

Sensor 122 is connected to electrometer 126 which senses small changes in current and translates amps to volts. Voltage signals from electrometer 126 are telemetry conditioned 128 and conveyed to transmitter 130 for radio transmission. All of the components within box 132 are implanted as a single unit in the patient.

Externally, radio signals from transmitter 130, indicative of glucose concentrations in the patient's blood, are transmitted to receiver 134. Receiver 134 may be connected to monitor 136 for data monitoring. The same receiver computer or another computer 138 may be used to analyze the raw data and generate glucose concentration information. A printer 140 connected to computer 138 generates hard copies of analyzed data.

Figure 8:
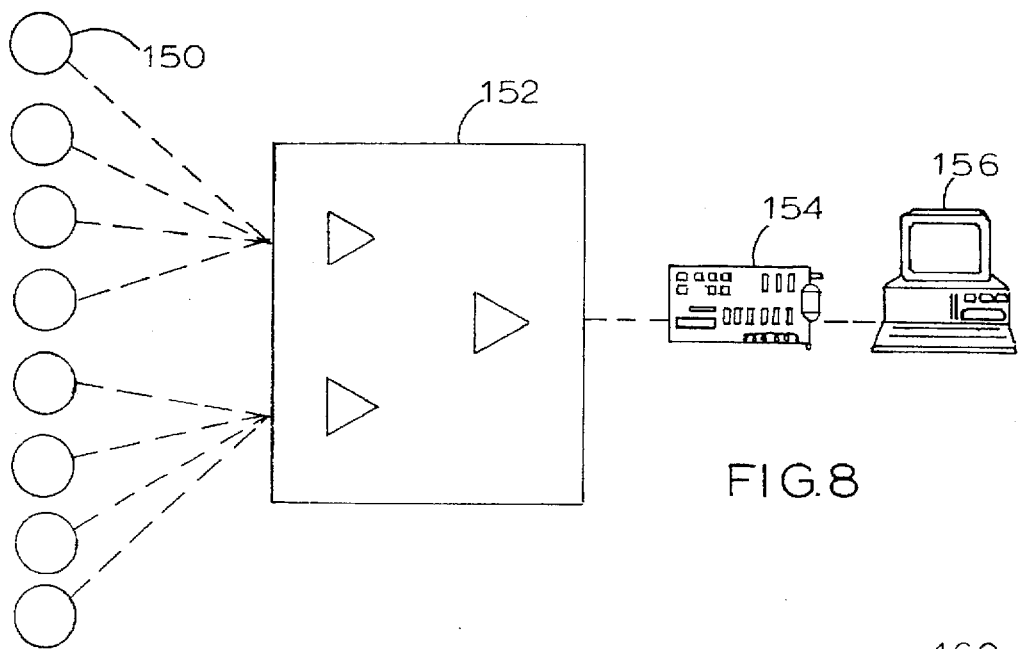
FIG. 8 is a flowchart of an analyte monitoring system including multiple sensors linked in parallel to the same data acquisition and processing components.

The concept of including multiple electrode pairs within a single sensor can be extended to an embodiment where separate sensors are implanted and commonly linked to a single electrometer as shown in FIG. 8. For example, eight implantable sensors 150 can be implanted in a patient and linked to a single electrometer 152 and transmitter (not shown). Transmitted signals are received by data acquisition adaptor 154 and acquisition computer 156. By increasing the number of sensors the overall precision, accuracy and longevity of the system can be greatly enhanced. If one or more anodes (or sensors) fails, the others still provide sufficient data sensing capacity so that the entire unit continues to perform satisfactorily. Various algorithms or averaging protocols can be used to process the multiple data streams.

Figure 9:
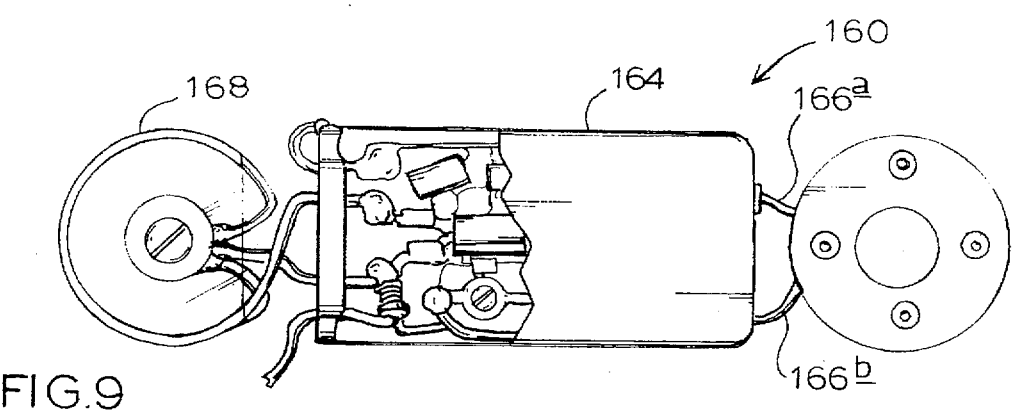
FIG. 9 is a top view of an implantable unit including a glucose sensor and radio telemetry device.

FIG. 9 shows schematically the components of an implantable unit in a glucose sensing system. Implantable unit 160 includes disc-shaped glucose sensor 162 which is connected to electrometer and telemetry conditioning package 164 via anode wire 166a and cathode wire 166b. Radio signals derived from the raw current signals are transmitted from transmitter element 168.

Circuitry

Figure 10:
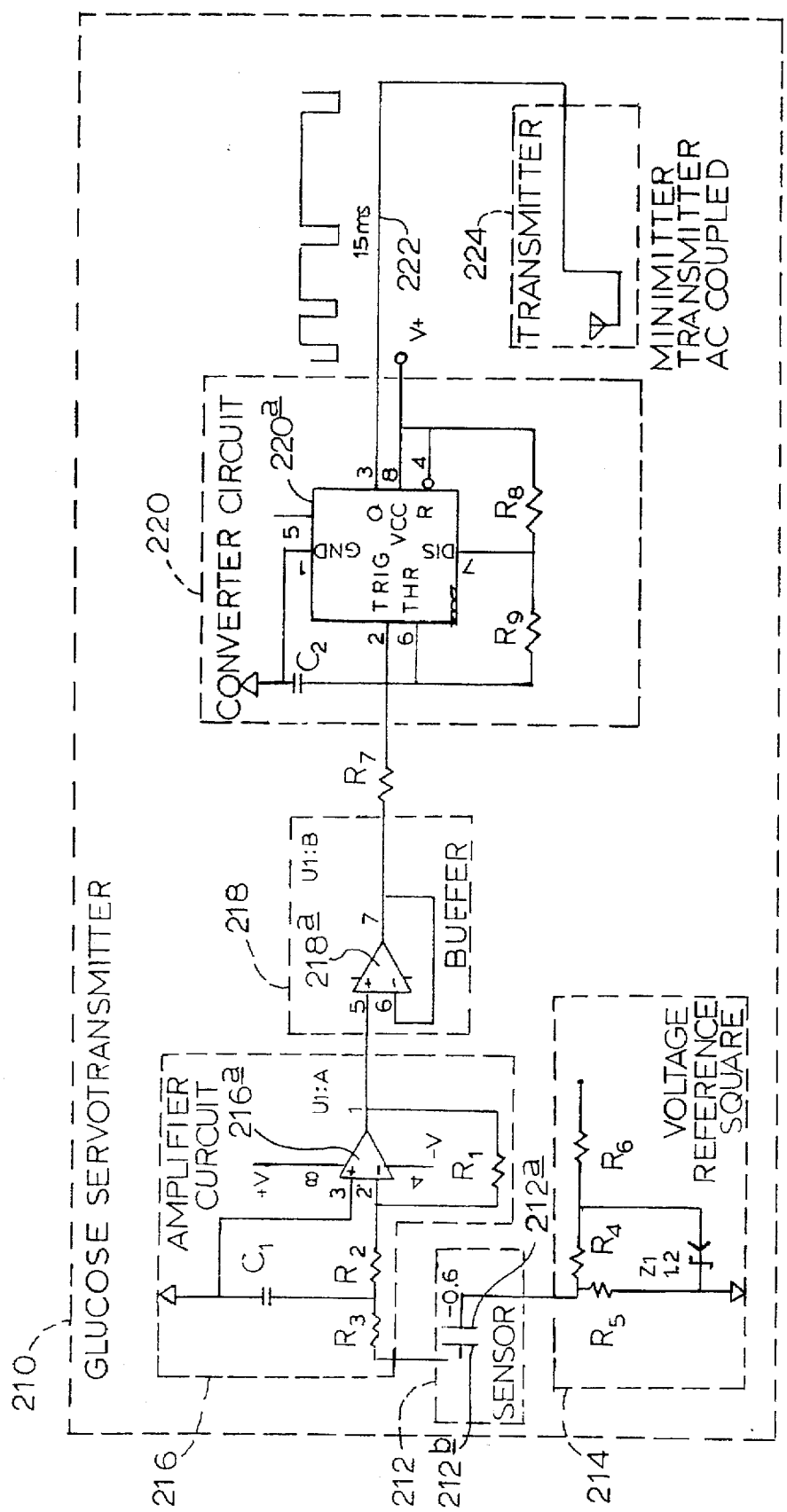
FIGS. 10 and 10A are circuit diagrams illustrating circuitry employed in glucose sensors of the present invention.

FIG. 10 shows custom circuitry structure employed in a glucose sensing system of the present invention. Shown generally at 210 is a glucose servotransmitter suitable for implementation with the present invention. Servotransmitter 210 is configured for transmission of data which is indicative of a sensed enzymatic reaction to a remote receiving source for subsequent processing, the sensing and conveyance of such data being described in detail below.

As shown, servotransmitter 210 includes a sensor 212 (also referred to as a two-electrode sensor) operatively connected between a voltage reference source 214 and an amplifier circuit 216. The output of circuit 216 is buffered at 218 and subsequently provided to a voltage-to-frequency circuit 220, which in the preferred embodiment includes a CMOS 7555 circuit indicated at 220a configured with a resistive and capacitative network which includes two resistors ($R_9$ and $R_8$) and a capacitor ($C_2$). Utilization of CMOS for designing circuit 220 has been found ideal due to its low power consumption aspects which results in longer battery life. The output terminal of circuit 220 is connected via line 222 to an AC-coupled transmitter 224 (also referred to herein as a minimitter) for transmission of data to an external receiving source.

Discussing the above servotransmitter in more detail, circuit 210 is configured for detecting electrons which are generated during an enzymatic reaction, and conveying data which is representative of such detected electrons to an external source for subsequent processing. More specifically, sensor 212 includes two electrodes, a cathode 212a and an anode 212b. Cathode 212a is connected to voltage reference source or circuit 214, and anode 212b is connected to amplifier circuit 216. Voltage reference circuit 214 is made up of three resistors $R_4$, $R_5$, and $R_6$ and a 1.2-volt Zener diode $Z_1$. Resistor $R_6$ is connected at one end to a negative voltage potential, and at the other end to diode $Z_1$ and resistor $R_4$. The other end of resistor $R_4$ is connected to resistor $R_5$, which in turn is connected to diode $Z_1$ as shown. The common node between resistors $R_4$ and $R_5$ is connected to cathode 212a.

Anode 212b is connected via resistors $R_3$, $R_2$, to the inverting terminal of amplifier 216a, and a capacitor $C_1$ is connected between resistors $R_3$, $R_2$ and ground. The non-inverting terminal of amplifier 216a is tied to ground. A resistor $R_1$ is connected between the output of amplifier 216a and its inverting terminal to provide negative feedback.

The output of amplifier 216a is connected to the non-inverting terminal of amplifier 218a, the output of which is connected to the inverting terminal in a voltage follower configuration for buffering the output of amplifier 216a. A resistor $R_7$ is connected between the output of amplifier 218a and the trigger terminal 2 of the CMOS 7555 circuit.

The CMOS 7555 is configured, with its attendant resistive and capacitative network, as a voltage-to-frequency converter whose output frequency is proportional to its input control voltage. Referring more specifically to the 7555, it may be seen that reset terminal 4 is connected to terminal 8, both of which are connected to a voltage potential which may be referred to as $V_{CC}$. A resistor $R_8$ is connected between reset terminal 4 and discharge terminal 7. A resistor $R_9$ is connected between discharge terminal 7 and the threshold terminal 6. A capacitor $C_2$ is connected between trigger terminal 2 and ground. Output terminal 3 is connected to the AC-coupled transmitter 224 for transmission of data to a remote location for processing.

Discussing the operation of the above-described glucose servotransmitter, it will be understood that voltage reference circuit 214 develops a potential of −0.6 volts which is used by sensor 212 to cause electrons produced in the vicinity of the sensor to flow, in the form of a generated current, with amplifier circuit 216, which includes operational amplifier 216a configured for feedback as described above. The output of amplifier 216a is a voltage which is buffered at 218 by operational amplifier 218a, the voltage output of which controls frequency for the trigger terminal of the CMOS 7555 through resister $R_7$ and frequency selection circuitry $C_2$, $R_8$, and $R_9$. The output terminal 3 of the CMOS 7555 is connected, via line 222, to transmitter 224 for transmission to an external source.

It will be appreciated that the above-described 7555 configuration converts the output of buffer 218 into a frequency which is determined by the voltage at threshold terminal 6. The 7555 serves two functions in the above configuration which are necessary for the transmission of sensed data to a remote location for processing. First, the 7555 provides a 15-msec pulse to key transmitter 224, thereby turning it on and off in accordance with practices which will be understood by those of skill in the art. Second, the 7555 is operable for voltage-to-frequency conversion, which is a measurement of sensor response. This dual function enables the aforementioned data transmission in a manner which will be understood by those of skill in the art.

Preferred component values (resistive and capacitative values) for the above-described servotransmitter 210 are as follows: (1) for voltage reference circuit 214: $R_4$=1 meg ohm; $R_5$=4.7 meg ohm; and, $R_6$=470 kohm; (2) for amplifier circuit 216: R1=500 meg ohm; $R_2$ and $R_3$=499 kohm; and, $C_1$=10 pf; (3) for converter circuit 220: $R_9$=180 kohm; $R_8$=1 meg ohm; and, $C_2$=1 microfarad; and, (4) $R_7$=4.7 meg ohm.

The above system is referred to as a "two-electrode" system because of the fact that two electrodes are utilized (the anode and the cathode) in the sensing of electrons produced during a particular enzymatic reaction. Another system which is suitable for sensing produced electrons and conveying data relative to such sensed electrons is a so-called "three-electrode" system which is shown in FIG. 10A and described briefly below.

Figure 10A:
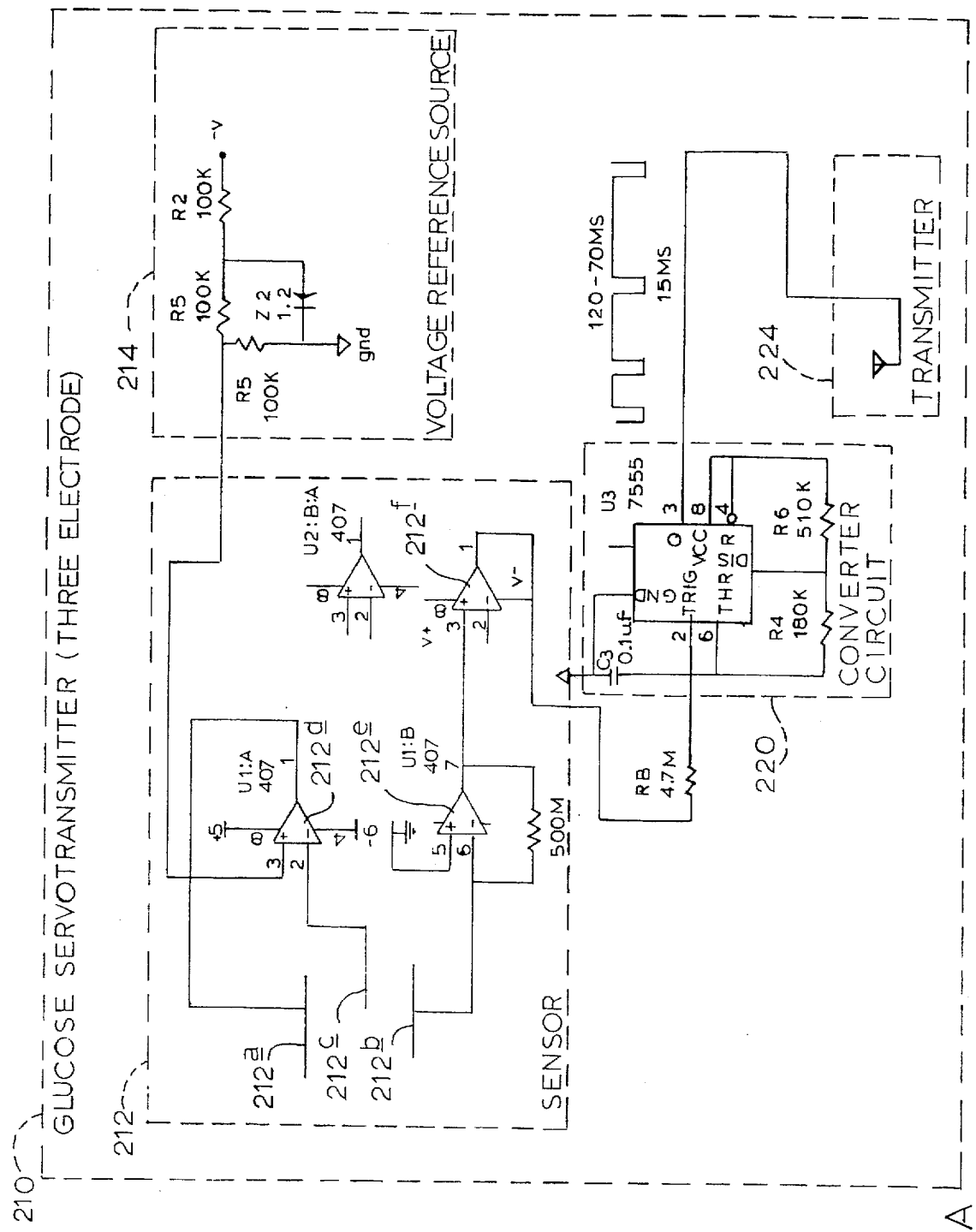

In FIG. 10A, like or similar elements of the three-electrode glucose servotransmitter 210 are labelled to correspond with the two-electrode elements appearing in FIG. 10. The Figure shows a sensor 212, a voltage reference source 214, a voltage-to-frequency converter circuit 220, and a transmitter 224. Voltage reference source 214, voltage-to-frequency converter circuit 220, and transmitter 224 will not be described because the operation of those elements is the same as, or similar to the operation of such elements as they appear in FIG. 10.

Sensor 212 in FIG. 10A varies somewhat from its FIG. 10 counterpart. Such variations take into account some observations regarding current and voltage control which have been made with respect to the two-electrode system described above, and improve somewhat, the control of such parameters. The three electrode sensor, set forth at 212, includes a counter electrode 212a (which may be formed from silver), a common return electrode 212b (also referred to as a working electrode and which may be formed from platinum), and a voltage probe 212c which may also be termed the reference electrode (and which also may be formed from platinum). Two operational amplifiers 212d, 212e are provided and operatively coupled to the electrodes as shown, in a configuration which provides greater current and voltage control which, in turn, assists in maintaining the integrity of the electrodes' sensitivity and the ability of the same to detect a produced current which is indicative of an enzymatic reaction. The control is effectuated in a damped, controlled manner.

The three electrode sensor 212 is shown in FIG. 10A. Amplifier 212d maintains a voltage which is the same as the reference voltage of −0.6 volts between the reference and working electrodes 212c, 212b respectively. This is accomplished by varying the current at the counter electrode 212a which is in the feedback loop of amplifier 212d. Amplifier 212e maintains the working electrode 212b at virtual ground converting the current to an output voltage, which is buffered at 212f and provided to CMOS 7555 converter circuit 220 for conversion from a voltage to a frequency (in a manner described above), the converter circuit thereafter triggering transmitter 224 is a pre-determinable fashion to transmit sensed data indicative of an enzymatic reaction to a remote location for processing.

Sensing Other Analytes

With minor modifications, the sensor designs described above may be used to detect analytes other than glucose. By changing the specific type of enzyme which covers the anode, the sensor can be used to measure many compounds. Several examples appear in Table 1 below.

TABLE 1

| ANALYTE | ENZYME |
| --- | --- |
| glucose | glucose oxidase |
| glucose | hexose oxidase |
| lactate | lactate oxidase |
| 1-methionine | 1-amino acid oxidase |
| 1-phenylalanine | 1-amino acid oxidase |
| d-aspartate | d-amino acid oxidase |
| d-glutamate | d-amino acid oxidase |
| urate | urate oxidase |
| ethyl alcohol | alcohol oxidase |
| methyl alcohol | alcohol oxidase |
| cholesterol | cholesterol oxidase |
| ascorbic acid | ascorbate oxidase |

In addition to measuring analytes in body fluids, sensors of the present invention can be used to measure the concentration of substrates in other fluids, for example, fruit and vegetable juices, wine, yogurt, etc.

Construction of a Glucose Sensor

A preferred sensor is constructed of epoxy resin in a disc shape, 1.3-centimeters in diameter and 0.2-centimeters in height. Four 36-gauge platinum wires terminate peripherally on one face of the disc (in holes drilled in the resin) and service hydrogen peroxide-sensing anodes. A solid silver cylinder, 0.7-centimeters outside diameter (the cathode), is secured by epoxy resin in the center of the disc. A layer of silver chloride can be deposited onto the surface of the silver by one of several processes. The sensor is preferably double-sided, which may be, for example, two of the four anode sensors configured "back-to-back", making a sensor composed of four anodes and one cathode on each face of the sensor.

Anode and cathode recording wires terminate in an amplifier and polarizing voltage source. An electrometer converts the current signal to a voltage signal and applies a constant polarizing voltage of 0.60 V to the electrodes. Output from the amplifier is routed both to a digital volt meter (Micronta 22-185A, Tandy Corp., Fortworth, Tex. 76102) and to a strip chart continuous chart recorder (Gould Instruments Model No. 11-2963-300, Valley View, Ohio 44126). The signal can also be routed directly into a computer by use of a data acquisition board. All of these electrical components can be miniaturized without altering the function.

A working 8-anode sensor (which has been demonstrated to respond to peroxide) then is selected for testing. The sensor is sanded, first with 600 and 1500 grit wet-or-dry, then followed by a polishing with 2000 grit wet-or-dry. The sensor is rinsed thoroughly in a stream of deionized water (DW) followed by blow drying in a cold nitrogen stream. The sensor is then immersed in an acetone bath and vigorously twirled for 20 seconds to remove any solvents or oils from the surface. The sensor is withdrawn from the acetone bath and is immediately rinsed in a DW stream. The sensor is again blown dry in a cold nitrogen stream, and continues to dry in room air for another 30 minutes.

If it is desired to include an interferent retarding layer, then a layer of PPX (or other suitable membrane material) approximately 5,000–8,000 Å thick is deposited directly on top of the anodes before depositing any enzyme.

The sanded, cleaned and dried sensor (with or without interferent retarding layer) is enzyme activated with a Glucose Oxidase (GO)—Bovine Serum Albumin (BSA)—Glutaraldehyde (CA) matrix prepared from mixing two parts GO+BSA (20 mg GO+5 mg BSA with 0.5 gram DW) plus one part GA (2.5% GA diluted with DW). Approximately 2.5 µl of this solution is applied via pipette directly to each anode. The solution is allowed to dry in room air for one hour. The sensor is then immersed in DW for 15 minutes to remove excess CA, rinsed briefly in a DW stream, and blown dry in a nitrogen stream. The sensor continues to dry in room air for one hour, after which spin-coating with PU (Tecoflex, Tecothane, Cook composite, or CAR) or vapor deposition with PPX (thickness =3000–5000 Å) is carried out.

Further miniaturization of the glucose sensor, as described above, will not adversely effect performance of the unit.

Testing, Connecting and Implanting Sensors

Sensors manufactured as described above, are tested the day after they are made by applying a polarizing voltage of 600 mV. The voltage output should stabilize after a one to two hour immersion in a temperature controlled PBS solution (37° C.) in the laboratory water bath. The sensor is tested in standard glucose solutions prepared by adding glucose to PBS so that the resulting test solutions (G=glucose), are concentrated in mg/dl as follows: G(0), G(100), G(200), G(300), G(400) and G(500); and in millimolar concentrations as follows: G(0), G(5.6), G(11.1), G(16.7), G(22.2) and G(27.8). The first data point is collected while the sensor is still immersed in PBS and represents the baseline output. After noting the output value, the sensor is moved to G(100) for ten minutes. The process of measuring the speed with which the sensor responds to the increase in glucose allows calculation of T90 (defined T90 below). The sensor is moved to the G(200) standard and the ten minute output value is collected from this standard. All of the following outputs are collected in ascending order in the same manner.

An implantable sensor has to satisfy three criteria: (1) it must have a T90 of less than three minutes; (2) it must be dose responsive in the glucose concentration range of 40–400 mg/dl; and (3) it must have adequate sensitivity. The T90 value is measured by using the continuous sensor readout provided by the data acquisition system. The point at which 90% of the maximum output is reached (after changing from the zero glucose level to the 100 mg/dl level) is recorded as the T90.

A sensor that is acceptable for implant must also be dose responsive, preferably substantially linear over the glucose concentration of 40–400 mg/dl. Minor to moderate non-linearities can be mathematically corrected to allow estimation of glucose level from sensor output data.

If a sensor meets all the previous criteria, it is attached to a transmitter. For example, a suitable transmitter may be obtained from Mini-Mitter which has a custom-built interface circuit between the transmitter and the sensor. The transmitter should have a battery pack which is fully charged.

The sensor can be implanted in the body of animals or humans. The sensor can be implanted subcutaneously, in an artery or vein, intramuscularly, intraperitoneally, in the brain or cerebrospinally. The preferred location is subcutaneous. The sensor can also be used in vitro, for example, in a laboratory to measure glucose concentration or other substrates or analytes in a liquid media.

The transmitter and sensor package are tested in vitro the day of the planned implant procedure. If the results are satisfactory (T90 less than 3 minutes, satisfactorily dose-responsive, adequate sensitivity), then the unit is sterilized, rinsed in sterile saline, and implanted subcutaneously in the recipient (after the appropriate preparation and anesthesia procedures).

Experiments

Experiment 1

We compared the performance of sensors with one anode to the performance of sensors with four anodes. Twelve one-sensor anode sensors were constructed substantially as described above. These sensors were similar to the ones shown in FIG. 1 except they only included one anode instead of four, and they only had electrodes on one side of the disc-shaped sensor. All sensors in this experiment were dip-coated with polyurethane (Cook Composites) instead of parylene. Twenty-four-anode sensors were constructed the same as the one-anode sensors except that they included four anodes on one face of the sensor substantially as shown in FIG. 1.

The sensors were implanted in rats. Glucose dose response data was collected for each of the sensors at frequent time points after implantation until the given sensor failed to perform satisfactorily. For each sensor, the last check point at which the sensor performed adequately, determined the functional life of that sensor.

Figure 11:
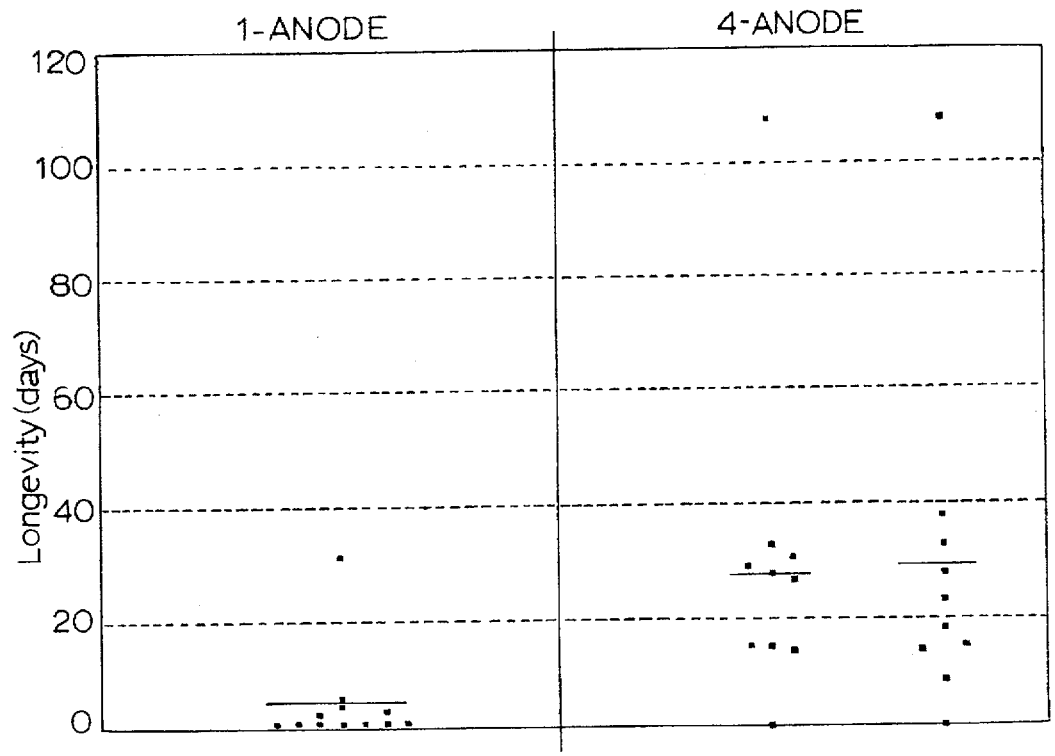
FIG. 11 is a graph demonstrating the results of an experiment conducted to compare longevity of single and multiple anode sensors.

FIG. 11 shows the results of this experiment. The average longevity for the one-anode sensors was about 4 days. In contrast, the average longevity for the four-anode sensors was about 28 days. This is a highly significant improvement in the functional life of an implanted glucose sensor, which we attribute to the increased number of anodes.

Experiment 2

The purpose of this experiment was to determine in vitro the performance capability in sensors which had failed in vivo. In this experiment, eight of the four anode sensors used in Experiment 1 were tested before implantation (pre-implant), and then tested again after eventually failing to perform and being removed (post-explant) from the rat.

Figure 12:
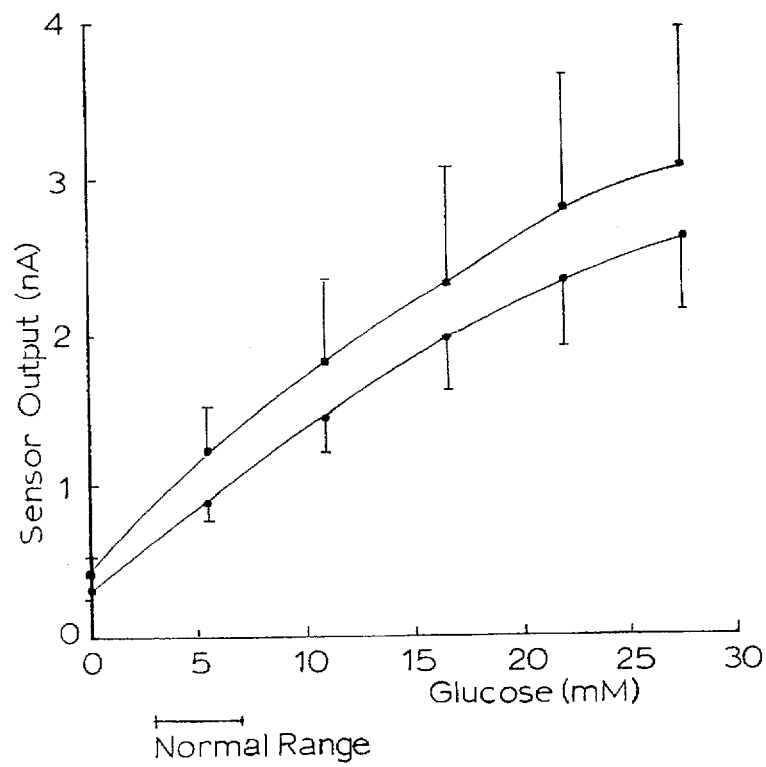
FIG. 12 is a graph illustrating the results of an experiment conducted to compare sensor performance pre-implant versus post-explant.

The results of the experiment are shown in FIG. 12. In FIG. 12 (and FIGS. 13 and 14), the "Normal Range" includes glucose concentrations which are typically observed in the normal population. The "Dynamic Range" includes the Normal Range plus abnormally high and low glucose concentrations which should be measurable with a glucose sensor. The results show that in vitro the sensors performed as well post-explant as they did pre-implant. This result demonstrates that failure of the sensors in vivo is not due to inactivation or loss of the glucose oxidase enzyme. We noted that over time in vivo a cellular coat tends to envelop the sensor. Before performing the post-explant testing on the sensors, the coats were removed. This suggests that the cellular coat which develops around the sensor may be involved with eventual sensor failure. Since the cellular coat is relatively non-uniform, it is possible to theorize that one of the reasons why longevity is increased with multiple anodes is that the probability of maintaining one or more anodes under a portion of the coat which is minimal enough so that the sensor still performs, is increased by increasing the number or surface area of sensing anodes.

Experiment 3

Figure 13:
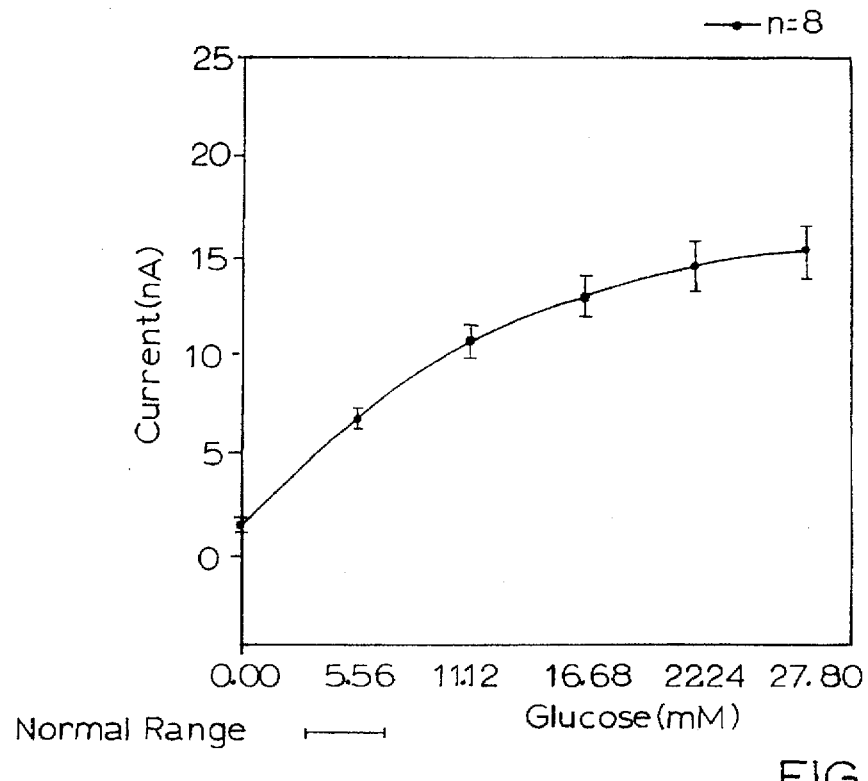
FIG. 13 is a graph showing the average glucose dose response and repeatability of eight sensors each of which was coated with PPX.

In Experiments 1 and 2, the sensors were dip-coated in polyurethane (Cook Composites). We subsequently discovered that uniformity and overall performance of the sensors can be improved by using PPX as the outer coat or semi-permeable membrane. The purpose of this experiment was to demonstrate glucose dose response and repeatability for eight sensors, each of which was coated with PPX at a thickness of approximately 3800 A. As shown in FIG. 13, we observed a dose response approaching linearity in the useful measurement range. Test repeatability was also improved with the PPX coated sensors, as shown by the smaller standard deviation margins in comparison to those shown in FIG. 12.

Experiment 4

Figure 14:
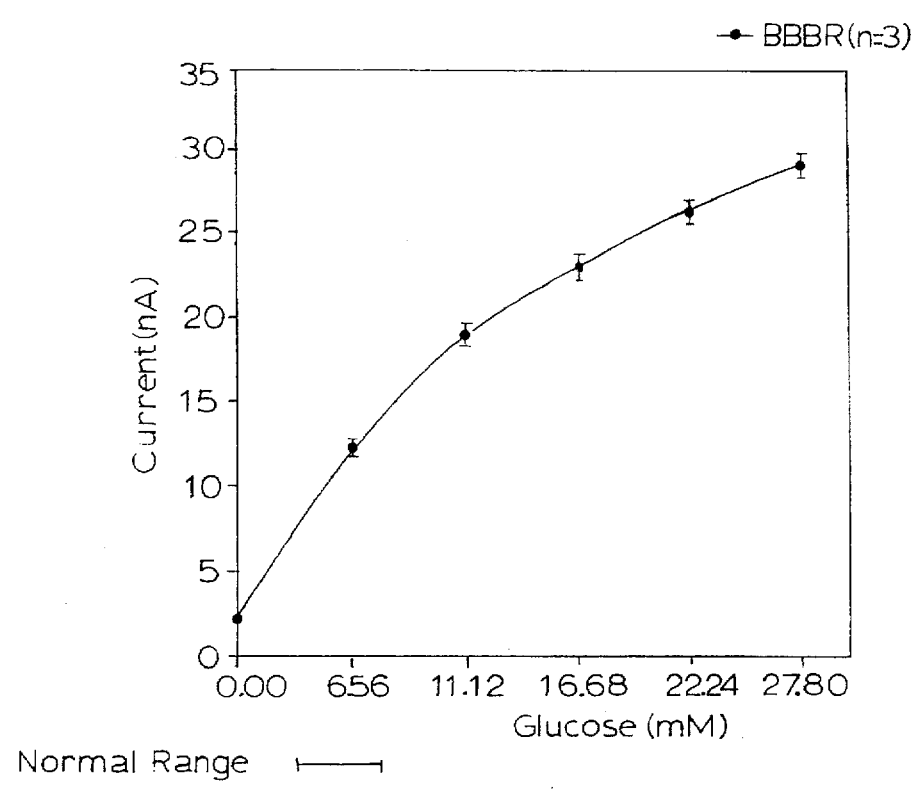
FIG. 14 is a graph showing the average glucose dose response and repeatability (n=3) for a sensor coated with CAR.

This experiment was similar to Experiment 3 except instead of using PPX as the semipermeable outer membrane, CAR was used. Eight-percent CAR was spin-coated over the surface of the sensor for 2.5 minutes at 4,000 RPM. The sensor was tested in vitro at various glucose concentrations in 3 successive runs. The data is shown in FIG. 14. The dose response over the useful measurement range approached linearity with a higher slope in comparison to slopes obtained with PPX and dip-coated sensors. We also noted a relatively small standard deviation on repeat tests with the CAR coated sensors.

Experiment 5

Figure 15:
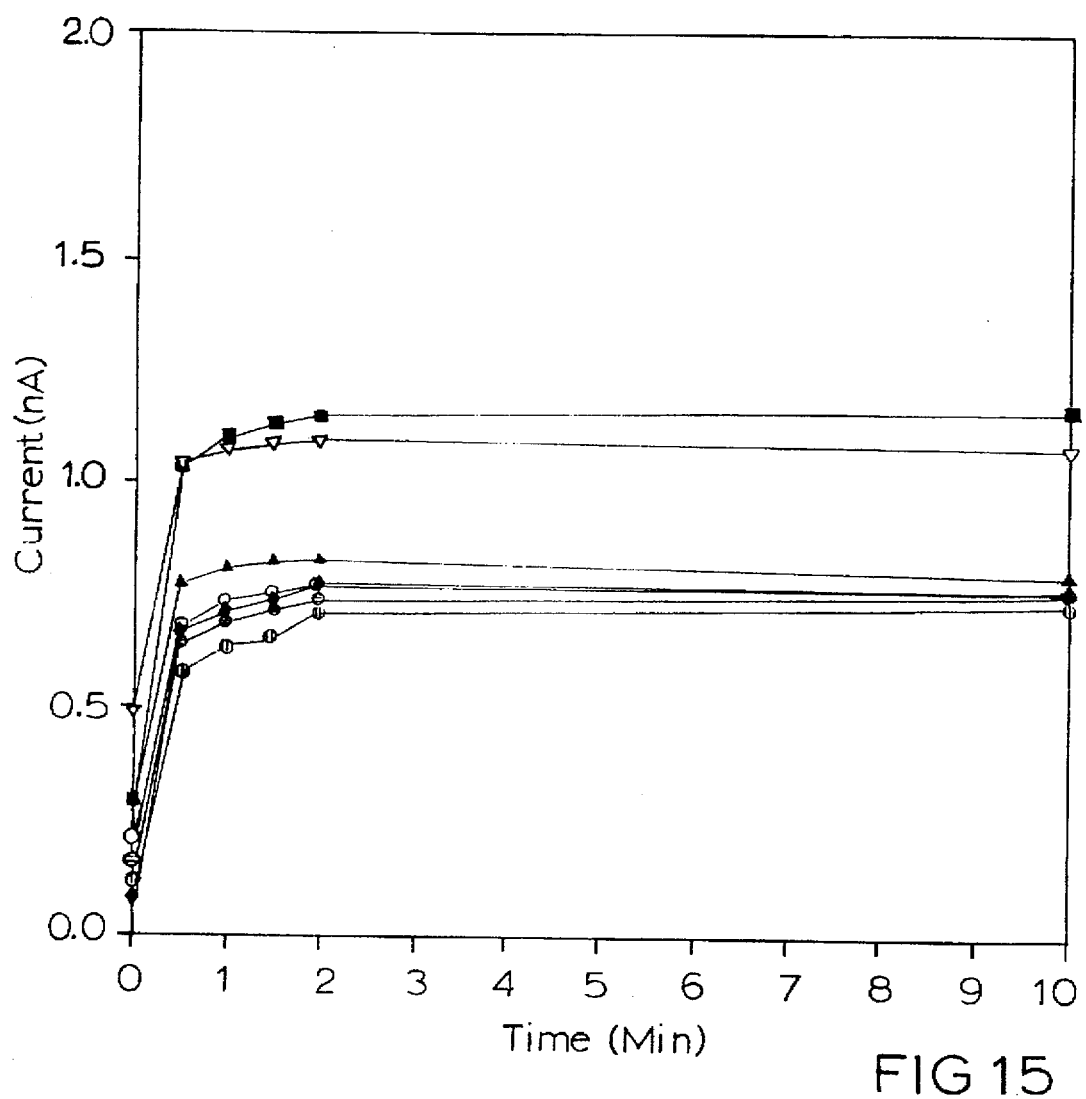
FIG. 15 is a graph presenting the results of an experiment conducted to determine the relative response times (T90s) for eight sensors each of which was coated with PPX.

This experiment was performed in vitro with PPX coated eight anode (four on each side) sensors to determine how rapidly the sensors respond to changes in glucose concentration (T90). Six sensors were constructed with PPX outer coats of 3000–5000 A. Results of this experiment are shown in FIG. 15. Each of the sensors responded with a T90, i.e., time to reach 90-percent of ultimate current output for a given change in glucose concentration, in less than one minute. This is a faster response time than we had observed previously with polyurethane dip-coated sensors.

We claim:

1. A device for electrochemically sensing changes in the concentration of an analyte of interest comprising an implantable sensor body having a pair of spaced facial expanses, each expanse of the body having at least one analyte-sensing electrode pair including an anode and a cathode spaced apart from each other and covered by a membrane which is semi-permeable to the analyte of interest, and an enzyme composition covering each anode of each analyte-sensing electrode pair, wherein the enzyme composition reacts specifically with the analyte of interest.

2. The device of claim 1 wherein the analyte of interest is glucose.

3. The device of claim 2 wherein the enzyme composition includes glucose oxidase and is located between the anode and the membrane.

4. The device of claim 3 wherein each expanse of the sensor body has an interferent retarding layer between the anode and the enzyme layer.

5. The device of claim 1 wherein the membrane comprises polyparaxylxylene.

6. The device of claim 1 wherein each expanse of the sensor body includes a plurality of anodes.

7. The device of claim 6 wherein each expanse of the sensor body has a plurality of electrode pairs, each electrode pair including one anode and one cathode.

8. The device of claim 7 wherein each expanse of the sensor body has four electrode pairs.

9. The device of claim 8 wherein the sensor body is disk-shaped.

10. A device for electrochemically sensing changes in the concentration of an analyte of interest comprising an implantable sensor body including a plurality of analyte-sensing electrode pairs, each electrode pair including an anode and a cathode, and a membrane comprising polyparaxylxylene or a carbonate-based polyurethane coveting the anodes.

11. The device of claim 10 further comprising a layer including glucose oxidase disposed between the anode and the membrane, wherein the device senses changes in glucose concentration of a fluid surrounding the device.

12. The device of claim 10 wherein the sensor body has two opposing sides, each side of the sensor body having at least one anode and at least one cathode.

13. The device of claim 12 wherein each side of the sensor body has a plurality of anodes.

14. The device of claim 13 wherein each side of the sensor body has a plurality of cathodes, each cathode being paired with one of the anodes.

15. A device for electrochemically sensing the concentration of an analyte of interest comprising an implantable sensor body supporting and defining multiple analyte detection sites, each site having an analyte-sensing electrode pair, each electrode pair including an anode and a cathode for generating signals indicative of analyte concentration at one of the sites on the sensor body.

16. The device of claim 15 wherein the sensor body has two opposing sides, the electrode pairs being distributed on both sides of the sensor body.

17. The device of claim 16 wherein the sensor body is disk-shaped.

18. The device of claim 16 wherein each side of the sensor body has at least four electrode pairs.

19. The device of claim 15 wherein the anodes lead to a common anode conductor and the cathodes lead to a common cathode conductor.

20. The device of claim 15 wherein the analyte of interest is glucose and each anode is covered with an enzyme layer comprising glucose oxidase.

21. The device of claim 15 wherein the sensor body has multiple sides, each side having an analyte detection site.

22. A device for electrochemically sensing the concentration of an analyte of interest comprising an implantable disk-shaped sensor body having two opposing facial expanses, each facial expanse containing at least one analyte detection site including an anode and a cathode covered by a membrane which is semi-permeable to the analyte of interest.

* * * * *

UNITED STATES PATENT AND TRADEMARK OFFICE
CERTIFICATE OF CORRECTION

PATENT NO. : 5,711,861
DATED : January 27, 1998
INVENTOR(S) : W. KENNETH WARD and ERIC S. WILGUS It is certified that error appears in the above-indentified patent and that said Letters Patent is hereby corrected as shown below:

Column 4, line 9, after "Chronoflex™" insert -- AR--.

Column 10, line 7, change "damped" to --clamped--.

Column 11, line 31, change "(CA)" to --(GA)--.

Column 11, line 38, change "CA" to --GA--.

Column 14, line 51, claim 10, change "coveting" to --covering--.

Signed and Sealed this

Ninth Day of November, 1999

Attest:

Q. TODD DICKINSON

Attesting Officer

Acting Commissioner of Patents and Trademarks